(12) United States Patent
Lee et al.

(10) Patent No.: US 8,771,716 B2
(45) Date of Patent: *Jul. 8, 2014

(54) MODIFIED RELEASE ANALGESIC SUSPENSIONS

(71) Applicant: McNeil-PPC, Inc., Skillman, NJ (US)

(72) Inventors: Der-Yang Lee, Flemington, NJ (US); Jen-Chi Chen, Morrisville, PA (US); Vincent Chen, Dayton, NJ (US); Robert Shen, North Wales, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/755,749

(22) Filed: Jan. 31, 2013

(65) Prior Publication Data

US 2013/0142846 A1    Jun. 6, 2013

Related U.S. Application Data

(63) Continuation of application No. 11/942,826, filed on Nov. 20, 2007, now Pat. No. 8,394,415.

(60) Provisional application No. 60/860,260, filed on Nov. 21, 2006.

(51) Int. Cl.
*A61K 31/785* (2006.01)

(52) U.S. Cl.
USPC ........................................ 424/400; 424/78.16

(58) Field of Classification Search
None
See application file for complete search history.

(56) References Cited

U.S. PATENT DOCUMENTS

| | | |
|---|---|---|
| 2,793,979 A | 5/1957 | Svedres |
| 3,185,626 A | 5/1965 | Claude |
| 3,485,719 A | 12/1969 | Rogovin |
| 4,221,778 A | 9/1980 | Raghunathan |
| 4,279,926 A | 7/1981 | Bruzzese et al. |
| 4,543,370 A | 9/1985 | Porter et al. |
| 4,643,894 A | 2/1987 | Porter et al. |
| 4,683,256 A | 7/1987 | Porter et al. |
| 4,725,441 A | 2/1988 | Porter et al. |
| 4,749,722 A | 6/1988 | Sunshine et al. |
| 4,752,580 A | 6/1988 | Downs |
| 4,788,220 A | 11/1988 | Mody et al. |
| 4,802,924 A | 2/1989 | Woznicki et al. |
| 4,828,841 A | 5/1989 | Porter et al. |
| 4,847,077 A | 7/1989 | Raghunathan |
| 4,863,741 A | 9/1989 | Becker |
| 4,873,231 A | 10/1989 | Smith |
| 4,906,478 A | 3/1990 | Valentine et al. |
| 4,975,465 A | 12/1990 | Motola et al. |
| 5,085,865 A | 2/1992 | Nayak |
| 5,183,829 A | 2/1993 | Caldwell |
| 5,275,822 A | 1/1994 | Valentine et al. |
| 5,358,502 A | 10/1994 | Herbig et al. |
| 5,374,659 A | 12/1994 | Gowan, Jr. |
| 5,409,907 A | 4/1995 | Blasé et al. |
| 5,424,075 A | 6/1995 | Daher et al. |
| 5,445,829 A | 8/1995 | Parradissis et al. |
| 5,510,385 A | 4/1996 | Stroppolo et al. |
| 5,595,758 A | 1/1997 | Adusumilli et al. |
| 5,621,005 A | 4/1997 | Gowan, Jr. |
| 5,630,871 A | 5/1997 | Jordan |
| 5,658,589 A | 8/1997 | Parekh et al. |
| 5,980,882 A | 11/1999 | Eichman |
| 6,001,392 A * | 12/1999 | Wen et al. ..................... 424/486 |
| 6,103,260 A | 8/2000 | Luber et al. |
| 6,149,943 A | 11/2000 | McTeigue et al. |
| 6,211,246 B1 | 4/2001 | Gelotte et al. |
| 6,228,398 B1 | 5/2001 | Devane et al. |
| 6,254,886 B1 | 7/2001 | Fusca et al. |
| 6,274,162 B1 | 8/2001 | Steffenino et al. |
| 6,365,184 B1 | 4/2002 | Depui et al. |
| 6,699,502 B1 | 3/2004 | Fanara et al. |
| 6,814,978 B2 | 11/2004 | Bunick et al. |
| 6,893,662 B2 | 5/2005 | Dittmar et al. |
| 6,902,742 B2 | 6/2005 | Devane et al. |
| 7,101,573 B2 | 9/2006 | Szymczak et al. |
| 7,157,100 B2 | 1/2007 | Doshi et al. |
| 2003/0099711 A1 | 5/2003 | Meadows et al. |
| 2004/0224020 A1 | 11/2004 | Schoenhard |
| 2005/0036977 A1 | 2/2005 | Gole et al. |
| 2005/0069580 A1 | 3/2005 | Hirsh et al. |
| 2005/0191349 A1* | 9/2005 | Boehm et al. ................. 424/464 |
| 2005/0249802 A1 | 11/2005 | Khanolkar et al. |

(Continued)

FOREIGN PATENT DOCUMENTS

| | | |
|---|---|---|
| CA | 2568443 | 12/2005 |
| EP | 0 225 615 A | 6/1987 |

(Continued)

OTHER PUBLICATIONS

Brabander ("Characterization of Ibuprofen as a Nontraditional Plasticizer of Ethyl Cellulose," Journal of Pharmaceutical Sciences, vol. 91, No. 7, Jul. 2002, pp. 1678-1685).*
International Search Report PCT/US2007/085166 dated Jul. 21, 2008.
Bodmeier, Roland et al.; "The effect of curing on drug release and morphological properties of ethylcellulose pseudolatex-coated beads", 1994, Marcel Dekker Inc., Drug Development and Industrial Pharmacy, vol. 20, No. 9, pp. 1517-1533.
De Brabander, C. et al., "Characterization of Ibuprofen as a Nontraditional Plasticizer of Ethyl Cellulose", 2002, Wiley-Liss Inc., Journal of Pharmaceutical Sciences, vol. 91, No. 7, pp. 1678-1685.

(Continued)

*Primary Examiner* — Suzanne Ziska
(74) *Attorney, Agent, or Firm* — Laura A. Donnelly (57) ABSTRACT

A pharmaceutical dosage form comprising non-steroidal-anti-inflammatory drugs, in particular propionic acid derivatives such as ibuprofen, along with a second active ingredient having a shorter therapeutically effective plasma concentration duration, such as phenylephrine, and methods of administering the same are provided. This method provides improved therapeutic effect, in particular pain relief along with decongestant relief, over extended time periods.

17 Claims, 4 Drawing Sheets

(56) References Cited

U.S. PATENT DOCUMENTS

| | | |
|---|---|---|
| 2006/0008527 A1 | 1/2006 | Lagoviyer et al. |
| 2006/0057205 A1* | 3/2006 | Srinivasan et al. ............ 424/472 |
| 2007/0122482 A1 | 5/2007 | Holm et al. |
| 2008/0020055 A1 | 1/2008 | Monteith et al. |
| 2008/0118571 A1 | 5/2008 | Lee et al. |

FOREIGN PATENT DOCUMENTS

| | | |
|---|---|---|
| EP | 0 564 154 A | 10/1993 |
| WO | WO 02/062299 A | 8/2002 |
| WO | WO 2006/017159 A | 2/2006 |
| WO | WO 2006/022996 A2 | 3/2006 |
| WO | WO 2008/064192 A2 | 5/2008 |

OTHER PUBLICATIONS

Wu, Chuanbin et al., "Non-traditional plasticization of polymeric films", 1999, Elsevier, International Journal of Pharmaceutics, vol. 177, pp. 15-27.

Drugs.com entry for "ibuprofen", retrieved from www.drugs.com on Jan. 19, 2011, pp. 1-5.

Drugs.com entry for "pseudoephedrine", retrieved from www.drugs.com on Jan. 19, 2011, pp. 1-4.

Drugs.com entry for "phenylephrine", retrieved from www.drugs.com on Jan. 19, 2011, pp. 1-6.

Drugs.com entry for "ibuprofen and pseudoephedrine", retrieved from www.drugs.com on Jan. 19, 2011, pp. 1-4.

Drugs.com entry for "Dristan Sinus", retrieved from www.drugs.com on Jan. 19, 2011, pp. 1-4.

Mashkovsky, M.D., "Medicines", 14$^{th}$ edition, M. 2001, vol. 1, p. 11.

Lachman, Leon et al., "The Theory and Practice of Industrial Pharmacy", Chapter 11, pp. 293-345 (1986).

USP 24-2000 Version, pp. 19-20 & 856 (1999).

Ansel, Howard C. et al.; "Pharmaceutical Dosage Forms and Drug Delivery Systems," 7$^{th}$ Ed. 1999, Lippincott, Williams & Wilkins, pp. 1-163 and 179-243.

Sweetman, Sean C.; "Martindale: The Complete Drug Reference," 33$^{rd}$ Ed. Pharmaceutical Press; 2002; pp. 1-90 and 1082-1102.

"Pharmaceutical Dosage Forms: Tablets", vol. 3, Chapters 2, 3, and 4, Ed. Lieberman and Lachman, (1982).

Dubernet et al. "Ibuprofen-loaded ethylcellulose microspheres: Analysis of the matrix structure by thermal analysis," Journal of Pharmaceutical Sciences. 80(1): 1029-1033 (1991).

Bodmeier, Roland; "Tablet of coated pellets," 1997, Elsevier, European Journal of Pharmaceutics and Biopharmaceutics, vol. 43, pp. 1-8.

Haslam, John L. et al.; "Tableting of Controlled release multiparticulates, the effect of millisphere size and protective overcoating," 1998, Elsevier, International Journal of Pharmaceutics, vol. 173, pp. 233-242.

Dashevsky, A. et al.; "pH-independent release of a basic drug from pellets coated with the extended release polymer dispersion Kollicoat® SR 30 D and the enteric polymer dispersion Kollicoat® MAE 30 DP," 2004, Elsevier, European Journal of Pharmaceutics and Biopharmaceutics, Vo. 58, pp. 45-49.

Leopold, Claudia S.; "A Practical Approach in the Design of Colon-specific Drug Delivery Systems," 2001, Wiley-VCH Verlag GmbH; Drug Targeting Organ-Specific Organ-Specific Strategies, Chapter 6, pp. 157-170.

Eccles, Ronald; "Substitution of phenylephrine for pseudoephedrine as a nasal decongestant. An illogical way to control methamphetamine abuse," 2006; Blackwell Publishing; British Journal of Clinical Pharmacology, vol. 63, No. 1, pp. 10-14.

Allen, Loyd V., et al.; "Ansel's Pharmaceutical Dosage Forms and Drug Delivery Systems," 2005, Lippincott, Williams & Wilkins, 8$^{th}$ ed., p. 247-253 & 339.

European Pharmacopeia, Monograph for "Phenylepherine" and "Phenylephrine Hydrochloride," 2005, Counsil of Europe, 5$^{th}$ ed., pp. 2231-2232.

Gavrilin, M.V. et al.; "Study of the interaction of ibuprofen with various polymers," 1999, Kluwer Academic/Plenum Publishers; Pharmaceutical Chemistry Journal, vol. 33, No. 11, pp. 604-606.

* cited by examiner

MODIFIED RELEASE ANALGESIC SUSPENSIONS

RELATED APPLICATION

This application claims priority to U.S. application Ser. No. 11/942,826, filed on Nov. 20, 2007, and to U.S. Application Ser. No. 60/860,260 filed Nov. 21, 2006, the entire contents of which are incorporated herein by reference.

The present invention relates to a modified release pharmaceutical formulation suitable for liquid dosage forms for the administration of at least two active ingredients. More specifically, the dosage form releases the active ingredients at rates that provide pharmaceutically suitable plasma concentrations of all of the active ingredients contained therein over a similar period of time.

BACKGROUND OF THE INVENTION

Therapeutic agents for treating pain, inflammation, and fever include analgesics, anti-inflammatories, and antipyretics. Non-steroidal anti-inflammatory drugs (NSAID's) are one type of such therapeutic agents. They include propionic acid derivatives, acetic acid derivatives, fenamic acid derivatives, biphenylcarbodylic acid derivatives, oxicams, and cyclooxygenase-2 (COX-2) selective NSAID's.

Propionic acid derivatives include for example ibuprofen, naproxen, and ketoprofen. Ibuprofen in particular is a widely used, well known NSAID possessing analgesic and antipyretic properties. It has been commercially available as an over-the-counter drug in many forms for several years. Ibuprofen is chemically known as 2-(4-isobutylphenyl)-propionic acid.

Immediate release NSAID's are typically administered about every 4 to 6 hours. Typically, a daily dose of NSAIDs range from about 50 to about 2000 milligrams, preferably from about 100 to 1600 and most preferably from about 200 to about 1200 milligrams.

Many other active ingredients are administered more frequently due to their relatively shorter duration. For example, the therapeutically effective plasma concentration of the decongestant phenylephrine is about 2.5 hours±0.7 hours, and thus it is typically administered every 2 to 4 hours.

In order to administer a single product containing an NSAID and another active ingredient having a pharmaceutically suitable plasma concentration that was shorter in duration, it would be necessary to control the release of the latter. It is well-known to reduce the rate of release of a drug or other active ingredient from a dosage form into the gastro-intestinal ("g.i.") fluids of a patient, especially in order to provide prolonged action of the drug in the body.

The rate at which an orally delivered drug reaches its site of action in the body depends on a number of factors, including the rate and extent of drug absorption into the blood through the g.i. mucosa. However, before a drug can be absorbed into the blood, it must first be dissolved in the g.i. fluids. For many drugs, absorption across the g.i. membranes is relatively rapid compared to their dissolution in the g.i. fluids, which thereby renders the dissolution of the drug as the rate limiting step in drug absorption. Therefore, a formulator may effectively control the rate of drug absorption into the blood by modifying the drug's rate of dissolution.

Because the onset and duration of the therapeutic efficacy of drugs vary widely, as do their respective absorption, distribution, metabolism, and elimination, it is known to modify the release of different drugs in different ways, or to have a first drug immediately released from the dosage form, while a second drug is released in a "modified" manner, e.g., either delayed or controlled.

Well known mechanisms by which a dosage form can deliver a drug at a modified rate (e.g. sustained, prolonged, extended or retarded release) include diffusion, erosion, and osmosis. It is often practical to design dosage forms that use a combination of the above mechanisms to achieve a particularly desirable modified release profile for a particular active ingredient.

Disadvantageously, many modified release applications employ solid dosage units having a final large size and weight. The administration of such dosage units presents a problem especially to those patients with difficulty swallowing, such as children and the elderly. Therefore, it is further desirable to provide such modified release medicines either in a chewable or orally disintegratable solid form or a liquid form. For many patients, liquid oral dosage forms are more preferred because they can be swallowed without the additional step of chewing.

Oral liquid forms have been commonly used for many years to deliver medication with an immediate release profile. See e.g., U.S. Pat. Nos. 5,374,659; 4,788,220; 4,975,465; and 5,183,829. However, the incorporation of a modified release medication into a liquid dosage form presents significant formulation challenges. In particular, coated or chemically bonded particles are typically employed to carry the modified release portion of the drug. For example, U.S. Pat. No. 5,980,882 discloses the use of a drug-resin complex along with a chelating agent for delaying the release rate of the drug. U.S. Pat. No. 4,847,077 discloses the use of water-permeable diffusion barrier coatings on drug-resin complex particles in order to provide a prolonged continuous release of the drug.

The properties of such particles, as well as those of the liquid vehicle for suspending them, must be compatible so that the particles can be maintained in a uniformly dispersed state. A particular challenge is the prevention of a premature release of drug from the suspended particles into the suspension medium during the storage life of the liquid dosage form prior to ingestion by a patient. Additionally, the maintenance of the desired dissolution profile as well as the desired dose uniformity of the liquid dosage form throughout its shelf-life are additional challenges to be addressed in formulating an oral, liquid modified release suspension product. Disadvantageously, these issues are often encountered when formulating a product containing, for example, an immediate release ibuprofen and a modified release second active ingredient, such as phenylephrine, due to the interaction between the ibuprofen and the modified release coating agents known in the art.

United States Patent Application 20060057205 discloses liquid dosage forms comprising phenylephrine and at least a second drug such as an analgesic, wherein the dosage form comprises particles of a complex of both drugs with an ion-exchange resin and wherein the particles are coated with a modified release coating such as a polymethacrylate. However, we have found that uncoated propionic acid derivatives such as ibuprofen can interact with semipermeable modified release coatings, such as those containing ethyl cellulose and polymethacrylate. Deleteriously, this interaction often compromises the release rate and the intended modified release properties of the coated drug.

Therefore, it would be desirable to have a modified release dosage form containing ibuprofen particles and modified release particles of another active ingredient, such as phenylephrine, which is not only palatable, but is also in a stable form that guarantees the required release profile after administration. In particular, it would further be desirable to have such an analgesic product that provided both an immediate release dose of the ibuprofen and a sustained release dose of the second active ingredient to the user without interaction between the ibuprofen and the sustained release coating.

SUMMARY OF THE INVENTION

The invention provides a pharmaceutical dosage form, such as a dosage form suitable for the administration of NSAIDS in a liquid suspension, said dosage form comprising, consisting of, and/or consisting essentially of:
a) a first portion containing first active ingredient, such as an NSAID, wherein the first active ingredient is released from the dosage form in a substantially immediate manner upon contact of the dosage form with a dissolution medium; and
b) a second portion containing
  i) ion exchange resin particles having a second active ingredient, which may be the same or different than the first active ingredient and in one embodiment may be as phenylephrine, bound thereon to form drug-resin complex particles;
  ii) a semi-permeable coating layer substantially covering each of said drug-resin complex particles; and
  iii) a protective coating layer substantially covering each of said particles in ii),
wherein the second active ingredient is released from the second portion in a modified release manner upon contact of the dosage form with the dissolution medium, and wherein the duration of the therapeutic effect of the second active ingredient as released from the second portion of the dosage form is substantially the same as the duration of the therapeutic effect of the first active ingredient, and methods for its administration as claimed herein.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

As used herein, the term "substantially covers" or "substantially continuous" means that the coating is generally continuous and generally covers the entire surface of the core or underlying layer, so that little to none of the active ingredient or underlying layer is exposed.

As used herein, "ATDAIRD" shall mean the average therapeutic duration of action of an effective immediate release dose" of a particular active ingredient. For example, the typical duration of action, i.e. period of therapeutic effect, of an immediate release dose of ibuprofen or ketoprofen is about 4 to about 6 hours. Accordingly, the ATDAIRD for ibuprofen or ketoprofen is 5 hours. The typical duration of action of an immediate release dose of naproxen is about 8 to about 12 hours. The ATDAIRD for naproxen, therefore is 10 hours. The typical duration of action of an immediate release dose of phenylephrine is about 2 to about 4 hours. The ATDAIRD for phenylephrine, therefore is 3 hours. The therapeutic duration of action of a particular active ingredient can readily be determined from the dosing instructions in the labeling for immediate release products containing that particular active ingredient.

As used herein, "modified release" shall apply to the altered release or dissolution of an active ingredient in a dissolution medium, such as g.i. fluids. The active ingredient or ingredients that may be released in a modified manner may be contained within, for example, dosage forms, coatings, or particles, or in any portion thereof, such as, for example, particles dispersed throughout a liquid suspending medium. Types of modified release include: 1) extended release; or 2) delayed release. In general, modified release dosage forms are formulated to make the active ingredient(s) available over an extended period of time after ingestion, which thereby allows for a reduction in dosing frequency compared to the dosing of the same active ingredient(s) in a conventional dosage form. Modified release dosage forms also permit the use of active ingredient combinations wherein the duration of one active ingredient may differ from the duration of another active ingredient.

By "extended release," it is meant that, after administration, an active ingredient is released from the dosage form in a substantially continuous, regulated manner, and the time for complete release, i.e. depletion, of the active ingredient from the dosage form is longer than that associated with an immediate release dosage form of the same. Types of extended release include controlled, sustained, prolonged, zero-order release, and the like.

By "delayed release," it is meant that, after administration, there is at least one period of time when an active ingredient is not being released from the dosage form, i.e. the release of the active ingredient(s) occurs at a time other than immediately following oral administration.

As used herein, "dissolution medium" shall mean any suitable liquid environment in which the suspension dosage form of the present invention can be dissolved, such as, for example, the in vitro dissolution media used for testing of the product, or gastro-intestinal fluids. Suitable in vitro dissolution media used for testing the dissolution of the active ingredient or ingredients from the suspension dosage form of the present invention include those described on page 786 of USP 23 (1995), which is incorporated by reference herein.

As used herein, "substantially coated" shall mean that less than about 20%, e.g. less than about 15%, or less than about 1.0% of the surface area of a particle is exposed, e.g. not covered, with a desired coating.

"Enteric" shall mean being able to be dissolved at a pH of greater than about 5.0 or greater than about 5.5 or greater than about 6.0 or that which is found in the intestines.

"Liquid dosage forms" may nonexclusively include suspensions or elixirs, wherein one or more of the active ingredients is dissolved, partially dissolved or in an undissolved or suspended state.

As used herein "drug-resin complex" shall mean the bound form of any of the active ingredients, including but not limited to the pharmaceutical active ingredients, and the ion exchange resin. The drug-resin complex is also referred to in the art as a "resinate".

As used herein, "immediate release" means that the dissolution characteristics of at least one active ingredient meets USP specifications for immediate release tablets containing that active ingredient. An active ingredient having an immediate release property may be dissolved in the gastrointestinal contents, with no intention of delaying or prolonging the dissolution of the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). Additionally, ibuprofen suspension may be analyzed for dissolution using pH 5.6 acetate buffer using USP apparatus 2 (paddles) at 50 rpm, where at least 80% of the ibuprofen contained in the dosage form is released therefrom within 60 minutes after dosing for an immediate release dose.

As used herein, a drug "release rate" refers to the quantity of drug released from a dosage form per unit time, e.g., milligrams of drug released per hour (mg/hr). Drug release rates are calculated under in vitro dosage form dissolution testing conditions known in the art. As used herein, a drug release rate obtained at a specified time "following administration" refers to the in vitro drug release rate obtained at the specified time following commencement of an appropriate dissolution test, e.g. those set forth in USP 24.

"Therapeutic effect," as used herein, shall mean any effect or action of an active ingredient intended to diagnose, treat, cure, mitigate, or prevent disease, or affect the structure or any function of the body.

"Semipermeable," as used herein, shall mean that water can pass through, and other molecules, including salts and the active ingredients described herein, are allowed to slowly diffuse through such a membrane when the membrane is in contact with an appropriate dissolution medium, e.g. gastrointestinal fluids or in-vitro dissolution media.

As used herein, "water insoluble" shall mean compositions that are substantially insoluble, practically insoluble or only slightly soluble in water as defined by U.S. Pharmacopeia, 24$^{th}$ edition. These compositions require at least about 100 parts of solvent per part of said composition, for complete dissolution.

"Erodible" as used herein shall mean the composition dissolves via surface erosion when in contact with an appropriate dissolution medium.

As used herein, the "protective coating" shall mean a coating that does not react with the other particles or other active ingredients in the dry vehicle, e.g. the matrix, of the dosage form or, in liquid dosage form embodiments, the liquid vehicle medium.

As used herein, the term "phenylephrine" means benzynemethanol, 3-hydroxy-α-[(methylamino)methyl], and includes, but is not limited to pharmaceutically acceptable salts, esters, isomers or derivatives thereof.

As used herein, a "particle" is a crystal, a granule, an agglomerate, or any undissolved solid material.

One embodiment of the present invention is directed to a modified release pharmaceutical dosage form suitable for the administration of active ingredients containing: a) an immediate release portion, e.g., a portion containing at least one active ingredient that is immediately released from the dosage form; and b) a modified release portion, e.g. a portion containing at least one active ingredient that is released into the bloodstream in a substantially continuous manner over a modified period of time.

In one embodiment, the active ingredient is released from the second portion in a modified release manner upon contact of the dosage form with the dissolution medium such that the modified release therapeutic effect of the second active ingredient as released from the second portion of the dosage form is substantially the same as the duration of the immediate release therapeutic effect of the first active ingredient. "Substantially the same as the duration of the immediate therapeutic effect of the first active ingredient," shall mean that the duration of therapeutic effect of the second active ingredient is the same as or within about 1 hour, i.e., e.g., within about ½ hour or within about 15 minutes or within about 10 minutes, of the duration of the first active ingredient. In another embodiment, the modified release therapeutic effect of the second active ingredient as released from the second portion of the dosage form may be, for example, at least from about 4 hours to about 6 hours, or from about 4 hours to about 8 hours, or from about 4 hours to about 12 hours, after initial administration of the dosage form.

The immediate release portion may contain one or more active ingredients that are dispersed at the molecular level, e.g. melted or dissolved, within the dosage form, or the active ingredient may be in the form of particles, which in turn may be coated or uncoated. In embodiments wherein the active ingredient is in form of particles, the particles (whether coated or uncoated) typically have an average particle size of from about 1 micron to about 2000 microns. In one embodiment, such particles are in the form of crystals having an average particle size of about 1 micron to about 300 microns. In another embodiment, the particles are in the form of granules or pellets having an average particle size of about 25 microns to about 2000 microns, for example, from about 25 microns to about 1000 microns or from about 25 microns to about 400 microns.

The modified release portion contains at least one active ingredient in a multiplicity of particles having modified release properties. In one embodiment, the core of these particles in the modified release portion may be comprised of the active ingredient in a pure, crystalline form, which is substantially coated with a modified release composition. Alternatively, the particle cores may be comprised of a mixture of granules comprised of one or more active ingredients with optional ingredients, such as binders, excipients and the like known in the art, and such granules are also substantially coated with a modified release composition. In another embodiment, the active ingredient particles may be dispersed throughout a matrix comprised of a modified release composition.

In yet another embodiment, one or more active ingredients may be chemically bound or "complexed" to a resin, e.g. an ion exchange resin, to form drug-resin complex particles (or active ingredient resin particles), which are first substantially coated with a semipermeable coating layer, then substantially coated with a protective coating layer. One skilled in the art would readily appreciate without undue experimentation that the particular ion exchange resin for use in this embodiment is dependent upon several factors such as, for example, the ionic charge of the active ingredient. An example of a suitable ion exchange resin for NSAID active ingredients includes, but is not limited to, styrene/divinyl benzene copolymers and cholestyramines, which are commercially available from Rohm & Haas under the tradename, "Duolite® AP143." An example of a suitable ion exchange resin for positively charged active ingredients, such as phenylephrine or pseudoephedrine, includes, but is not limited to, an sulfonic acid cationic ion exchange resin derived from a sulfonated styrene/divinyl benzene copolymer, such as those commercially available from Rohm & Haas under the general tradename "Amberlite," e.g., "Amberlite IRP69," and those commercially available from Dow Chemical Company, sold under the tradename, "Dowex," e.g., "Dowex Marathon," "Dowex Monosphere," and "Dowex XYS-40010.00." The Amberlite IRP 60 and Dowex XYS-40010.00 products are sulfonated polymers comprised of polystyrene cross-linked with about 8% of divinylbenzene, with an ion exchange capacity of about 4.5 to 5.5 meq./g of dry resin (H+-form). The Amberlite IRP-69 product is comprised of irregularly-shaped particles with a particle size range of about 47 μm to about 149 μm, whereas the Dow XYS-40010.00 product is comprised of spherical particles with a particle size range of about 45 μm to about 150 μm. Another suitable ion exchange resin, "Dow XYS-40013.00," is a polymer comprised of polystyrene cross-linked with about 8% of divinylbenzene and functionalized with a quaternary ammonium group; its exchange capacity is normally within the range of about 3 to about 4 meq./g of dry resin. Another suitable ion exchange resin includes polacrilin potassium, which is also known as methacrylic acid polymers with divinylbenzene potassium salt. Suitable examples of polacrin potassium include, but are not limited to those commercially available from Rohm & Haas under the tradename, "Amberlite IRP-64," which is a cationic ion exchange resin that is derived from a copolymer of methcrylic acid and divinyl benzene. Additional details of complexation with polymeric resins are well known in the art and disclosed in, for example, U.S. Pat. Nos. 4,221,778; 5,980,882; 4,847,077; and 6,001,392.

Ion exchange resins are generally classified into various types, including strong acid cations, strong base cations, weak acid cations and weak base cations. In general, the drug is mixed with an aqueous suspension of a suitable resin, and the resin-drug complex is then washed and dried. Binding of the drug onto the resin may be demonstrated by analyzing the pH of the media eluting from the wash or by measuring a change in sodium concentration of the wash.

In embodiments wherein it is desirable to bind phenylephrine to an ion exchange resin via an aqueous mixture, the phenylephrine hydrochloride (PHE-HCl) and the resin may first be combined into a mixture. Then, the sodium ion of the resin may be exchanged with the protonated form of phenylephrine (PHE-H$^+$). Typically, the resulting drug-resin complex has a weight ratio of phenylephrine to resin of about 20:80 to about 80:20, i.e., e.g. from about 30:70 to about 70:30.

In one particular embodiment, the modified release portion of the dosage form is substantially free of ion exchange resins. By "substantially free of ion exchange resins," it is meant that the amount of ion exchange resin, based upon the total weight of all active ingredient particles in the dosage form, is less than about 1 percent, e.g., less than about 0.5 percent or less than about 0.1 percent.

In accordance with the present invention, the drug-resin complex particles are substantially coated with a semipermeable coating. By "substantially coated," it is meant that about 80%, e.g., about 85% or about 99% of the particle surface is coated.

Examples of suitable semipermeable coatings include but are not limited to, polymers such as cellulose acetate, ethylcellulose, non-enteric polymethacrylates and copolymers and mixtures thereof. Exemplary non-enteric polymethacrylates include, but are not limited to, poly(ethyl acrylate, methyl methacrylate) 2:1, which is commercially available from Rohm Pharma under the tradename, "EUDRAGIT NE"; poly (methyl acrylate, methyl methacrylate, methacrylic acid) 7:3:1 which is commercially available from Rohm Pharma under the tradename "EUDRAGIT FS;" poly(ethyl acrylate, methyl methacrylate, triethylammonioethyl methacrylate chloride) 1:2:0.2, which is commercially available from Rohm Pharma under the tradename "EUDRAGIT RL"; poly (ethyl acrylate, methyl methacrylate, triethyleammonioethyl methacrylate chloride 1:2:0.1, which is commercially available from Rohm Pharma under the tradename "EUDRAGIT RS," and copolymers and mixtures thereof. Cellulose acetate, which is also known in the art under the general terms of acetyl cellulose, cellulose diacetate, and cellulose triacetate, is commercially available from the Eastman Chemical Company. Ethylcellulose, which is also known in the art as cellulose ethyl ether, is commercially available from the Dow Corporation under the tradename "ETHOCEL." In one embodiment, the semipermeable coating may be selected from cellulose acetate, ethylcellulose, and mixtures thereof.

The coated drug-resin complex particles are then substantially coated with a protective coating. By "substantially coated," it is meant that about 80%, e.g., about 85% or about 99% of the coated particle surface is then coated with a protective coating layer.

Examples of suitable protective coatings include those comprised of enteric polymers including, but not limited to hydroxypropyl methylcellulose phthalate (also known as hypromellose phthalate), hydroxypropyl methylcellulose acetate succinate, cellulose acetate phthalate, polyvinylacetate phthalate, shellac, enteric polymethacrylate-based polymers, and copolymers and mixtures thereof. Examples of suitable enteric polymethacrylate-based polymers include, but are not limited to poly(methacrylic acid, methyl methacrylate) 1:2, which is commercially available from Rohm Pharma GmbH under the tradename, "EUDRAGIT S" polymers; poly(methacrylic acid, methyl methacrylate) 1:1, which is commercially available from Rohm Pharma GmbH under the tradename, "EUDRAGIT L-100, L-30D, L 12.5 and L 12.5 P" polymers; and poly(methacrylic acid, ethyl acrylate) 1:1 which is commercially available from Rohm Pharma under the tradename "EUDRAGIT L30-D 55 and L-100-55," from Eastman Chemical under the tradename "Eastacryl 30D," from Colorcon Corporation under the tradename, "Acryl-EZE" and from BASF Fine Chemicals under the tradename, "Kollicoat MAE 30D." In one embodiment, the enteric polymer may be selected from non-acrylate compounds, such as hydroxypropyl methylcellulose phthalate, hydroxypropyl methylcellulose acetate succinate, cellulose acetate phthalate, polyvinylacetate phthalate, shellac and copolymers and mixtures thereof.

In one embodiment, the protective coating may also be provided in the form of a lipid, such as a fatty acid ester, a wax, or mixtures thereof. Examples of suitable fatty acid esters include, but are not limited to sucrose fatty acid esters; mono-di- and triglycerides; glyceryl behenate; glyceryl palmitostearate; glyceryl tristearate; glyceryl trilaurylate; glyceryl myristate; GLYCOWAX-932; lauroyl macrogol-32 glycerides; stearoyl macrogol-32 glyceride; fatty acid esters such as those having a fatty acid chain length of about $C_{10}$-$C_{40}$; and mixtures thereof.

Examples of suitable waxes include, but are not limited to carnauba wax, spermaceti wax, beeswax, candelilla wax, shellac wax, carnuba wax, beeswax, microcrystalline wax, and paraffin wax and the like, and mixtures thereof.

Optionally, the semi-permeable coating and/or the protective coating may include a plasticizer. Examples of suitable plasticizers include, but are not limited to, polyethylene glycol; propylene glycol; glycerin; sorbitol; triethyl citrate; tributyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; glycerol monostearate; hydrogenated castor oil; substituted triglycerides and glycerides; and mixtures thereof.

In one embodiment, a suitable plasticizer may be used in an amount, based upon the total dry weight of the semi-permeable coating, from about 0.1% to about 40%, e.g. about 1% to about 30% or from about 5% to about 20%.

In one embodiment, a suitable plasticizer may be used in an amount, based upon the total dry weight of the protective coating, from about 0.1% to about 40%, i.e., e.g., from about 1% to about 30% or from about 5% to about 20%.

In one embodiment, the weight ratio of the semipermeable coating layer to the protective, enteric coating layer in the modified release particles is about 10:90 to about 90:10, or about 20:80 to about 80:20.

In one embodiment, the modified release particles are substantially free of enteric polymers, i.e., e.g. the modified release particles contain, based upon the total weight of the modified release particles, less than about 1 percent or less than about 0.25 percent of enteric polymers.

In one embodiment, the drug-resin complex may be treated with a solvating or impregnating agent that is added while the active ingredient and the resin are being mixed or after the active ingredient is bound to the resin. Examples of suitable impregnating agents include, but are not limited to, sorbitol, polyethylene glycol, glycerol, propylene glycol, mannitol, lactitol, lactose, methylcellulose, and mixtures thereof. The impregnating agent may be present in an amount of about 5 parts to about 50 parts per weight of the dry resin.

In one embodiment, a chelating agent may be added to the dosage form in order to stabilize the drug-resin complex by inhibiting the oxidation of the drug-resin complex. Suitable chelating agents include, but are not limited to, ethylenediaminetetraacetic acid (EDTA) and salts of EDTA including, but not limited to, edetate calcium disodium, edetate trisodium, edetate disodium, and edetate sodium. The chelating agent may be present in an amount of about 0.005 percent to about 10 percent by weight of the final dosage form.

The active ingredient-resin complex particles, which contain a first semipermeable coating layer underneath a second protective coating later, yield a modified release composition that contains, based upon the total dry weight of such modified release composition, from about 1 percent to about 99 percent, e.g. from about 5 percent to about 80 percent of the first semipermeable coating layer and from about 5 percent to about 99 percent, e.g. from about 10 percent to about 90 percent of the second protective coating layer.

The thickness of each of the two coating layers may vary depending upon the modified release properties desired, the active ingredient selected, and the like, but typically may range from about 0.01 microns to about 500 microns, e.g., from about 0.1 microns to about 100 microns.

The dry weight per surface area of the first coating layer on the particles is about 0.1 mg/cm$^2$ to about 10 mg/cm$^2$, i.e., e.g. from about 0.5 mg/cm$^2$ to about 5 mg/cm$^2$. The dry weight per surface area of the second coating layer on the particles is about 0.1 mg/cm$^2$ to about 10 mg/cm$^2$, e.g. about 0.5 mg/cm$^2$ to about 8 mg/cm$^2$.

The weight gain of the active ingredient-resin complex particles after the addition of the first semipermeable coating layer thereto is, based upon the dry weight of the uncoated, active ingredient-resin complex particles, from about 1 percent to about 200 percent, e.g., from about 20 percent to about 150 percent. The weight gain of the active ingredient-resin complex particles after the addition of the second protective coating layer is, based upon the dry weight of the active ingredient-resin complex particles coated with the first semipermeable coating layer, from about 25 percent to about 400 percent, e.g., from about 40 percent to about 400 percent.

The coated active ingredient particles may be formed by any suitable method known in the art. Suitable particle forming and coating methods include high sheer granulation, fluid bed granulation, e.g. rotor granulation, fluid bed coating, wurster coating, coaccervation, spray drying, spray congealing, and the like and are described for example in Pharmaceutical Dosage Forms: Tablets Volume 3, edited by Herbert A. Lieberman and Leon Lachman, Chapters 2, 3, and 4 (1982).

In one embodiment wherein the particles are formed by binding the active agent to an ion exchange resin to form a drug-resin complex, the resulting complex particles are first coated with the semipermeable layer using wurster fluid bed coating, then coated using wurster fluid bed coating with an enteric layer. The coating materials may be sprayed onto the particles via a solution or dispersion containing solvents including but not limited to water, ethanol, methanol, acetone, hexane, cyclohexane, methylene chloride, isopropanol, and mixtures thereof. See e.g., U.S. Pat. No. 4,847,077.

In one embodiment the average diameter of the drug-resin complex is from about 20 microns to about 400 microns, or about 20 microns to about 300 microns. In one embodiment, the average diameter of the drug-resin complex particles coated with the first coating layer is from about 20 to about 800 microns, e.g. from about 50 microns to about 400 microns, and the average diameter of the drug-resin complex particles coated with both the first and second coating layers is from about 50 to about 1000 microns, e.g. from about 100 microns to about 400 microns.

The dosage form of the present invention contains one or more active agents or ingredients. Suitable active ingredients broadly include, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

In one embodiment of the invention, at least one active ingredient may be selected from bisacodyl, albuterol, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, at least one active ingredient is selected from analgesics, anti-inflammatories, and antipyretics, e.g. non-steroidal anti-inflammatory drugs (NSAIDs), including a) propionic acid derivatives, e.g. ibuprofen, naproxen, ketoprofen and the like; b) acetic acid derivatives, e.g. indomethacin, diclofenac, sulindac, tolmetin, and the like; c) fenamic acid derivatives, e.g. mefenamic acid, meclofenamic acid, flufenamic acid, and the like; d) biphenylcarbodylic acid derivatives, e.g. diflunisal, flufenisal, and the like; e) oxicams, e.g. piroxicam, sudoxicam, isoxicam, meloxicam, and the like; f) cyclooxygenase-2 (COX-2) selective NSAIDs; g) aspirin and h) pharmaceutically acceptable salts of the foregoing.

In one particular embodiment, at least one active ingredient is selected from propionic acid derivative NSAID, which are pharmaceutically acceptable analgesics/non-steroidal anti-inflammatory drugs having a free —CH(CH₃)COOH or —CH₂CH₂COOH or a pharmaceutically acceptable salt group, such as —CH(CH₃)COO—Na+ or CH₂CH₂COO—Na+, which are typically attached directly or via a carbonyl functionality to a ring system, preferably an aromatic ring system.

Examples of useful propionic acid derivatives include ibuprofen, naproxen, benoxaprofen, naproxen sodium, fenbufen, flurbiprofen, fenoprofen, fenoprofen calcium, flurbiprofen, tiaprofenic, oxaprozin, fenbuprofen, ketoprofen, indoprofen, pirprofen, carprofen, oxaprofen, pranoprofen, microprofen, tioxaprofen, suprofen, alminoprofen, tiaprofenic acid, fluprofen, bucloxic acid, and pharmaceutically acceptable salts, derivatives, and combinations thereof.

In one embodiment of the invention, the propionic acid derivative is selected from ibuprofen, ketoprofen, flubiprofen, and pharmaceutically acceptable salts and combinations thereof.

In another embodiment, the propionic acid derivative is ibuprofen, 2-(4-isobutylphenyl) propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

In another particular embodiment of the invention, at least one active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another particular embodiment of the invention, at least one active ingredient may be selected from pseudoephedrine, phenylephrine, phenylpropanolamine, chlorpheniramine, dextromethorphan, diphenhydramine, clofedianol, astemizole, terfenadine, fexofenadine, loratadine, desloratadine, cetirizine, mixtures thereof and pharmaceutically acceptable salts, esters, isomers, and mixtures thereof.

In a particular embodiment the active ingredient that is bound to a resin complex is selected from phenylephrine, pseudoephedrine, dextromethorphan, diphenhydramine, chlorpheniramine and mixtures thereof. In one embodiment the resin based particles are bound using hydrochloride and hydrobromide salts of phenylephrine, pseudoephedrine, dextromethorphan, diphenhydramine, chlorpheniramine, and mixtures thereof.

In another particular embodiment, at least one active ingredient is an NSAID or a pharmaceutically acceptable salts thereof, and the other active ingredient bound to the drug resin complex is phenylephrine and/or psuedoephedrine.

In one embodiment, a therapeutically effective amount of the active ingredient or ingredients may be present in a "unit dose volume," which can be in the form of a powder or an aqueous suspension. "Therapeutically effective amount," as used herein, is an amount of active ingredient that produces the desired therapeutic response upon oral administration. One skilled in the art can readily determine the "therapeutically effective amount" of an active ingredient for a given patient by considering factors such as, for example, the particular active ingredient being administered; the bioavailability characteristics of the active ingredient; the dose regimen desired; the age and weight of the patient; and the like. As used herein, a "unit dose volume" may be any convenient volume for orally administering a dose of a given product to a patient.

In this embodiment, the "unit dose volume" is typically accompanied by dosing directions, which instruct the patient to take an amount of the active ingredient that may be a multiple of the unit dose volume depending on, e.g., the age or weight of the patient. Typically the unit dose volume of the suspension will contain an amount of active ingredient that is therapeutically effective for the smallest patient. For example, suitable unit dose volumes may include one teaspoonful (about 5 mL), one tablespoonful (about 15 mL), one dropper, or one milliliter.

According to the invention, a dosage form containing NSAID may be provided to a mammal in need of treatment, in particular pain relief treatment, in a single administration that provides for the release of the active ingredient in the blood over an extended time period, e.g. over about an 4 hour or about a 6 hour period. At time zero, an initial dose of the NSAID is provided, i.e. administered, to the mammal via of the active ingredient(s) in the immediate release dose portion. The second active ingredient is then released into the blood throughout about the next four to about 6 hours from initial administration of the formulation containing the active ingredient via the active ingredient(s) in the modified release dose portion. In other words, the formulation still retains undissolved, second active ingredient after about four or about six hours from initial administration.

In practicing the present invention, the dosage form may be comprised of, based upon the total weight of the active ingredient, from about 0.01 percent to about 40 percent of an immediate release dose particle portion of the first active ingredient; and from about 0.01 percent to about 40 percent, i.e., from about 0.01 percent to about 10 percent of a modified release dose portion of the dual coated second active ingredient. As used herein, "portion" shall mean the amount of the identified active ingredient along with any optional components, but shall not include the liquid vehicle or, in solid dosage forms, the matrix or other dry vehicle into which the immediate release dose particles may be combined. The immediate release dose portion and the modified release dose portion may be combined with an appropriate vehicle to form either: 1) a dry mixture that can be suspended extemporaneously when needed; 2) a ready-to-use liquid dosage form, such as an elixir or suspension; or 3) a solid or semi solid dosage form.

Suitable constituents of the vehicle can include, without limitation, solvents; structuring agents; swelling agents; surfactants; sugars; buffering substances such as citric acid and sodium citrate; glycine and hydrochloric acid, sodium phosphate, and potassium phosphate; preservatives and bacteriostatic agents such as esters of p-hydroxybenzoic acid; colorants; and various flavorings and sweeteners commonly used in pharmaceuticals.

Examples of suitable sweeteners include, but are not limited to any known sweetening agent such as sugars, sugar alcohols, high intensity sweeteners, and mixtures thereof. Suitable sugars include, but are not limited to sucrose, dextrose, high fructose corn syrup, and maltose. Suitable sugar alcohols include, but are not limited to sorbitol, xylitol, and mannitol. Suitable high intensity sweeteners include, but are not limited to sucralose, aspartame, saccharin, and acesulfame K.

In one embodiment, an effective amount of a buffering agent is used in order to have the pKa of at least one active ingredient contained in the modified release portion of the liquid suspension dosage form be greater than the pH of the overall liquid suspension dosage form.

In addition, the vehicle may also be comprised of water, or mixtures of water and a pharmaceutically acceptable water-miscible co-solvent known in the art such as, for example, glycols, alcohols and glycerol.

In certain embodiments the dosage form may include any suspending systems known in the art, such as those that typically include one or more structuring agents and/or one or more swelling agents. In one embodiment, the dosage form contains, based upon the total weight of the liquid suspension dosage form, from about 0.1 percent to about 10 percent, of a suspending system. Suitable suspending systems include those disclosed in, for example, U.S. Pat. Nos. 5,374,659, 5,621,005, and 5,409,907, which are all incorporated by reference herein in their entireties.

Structuring agents that are suitable for use in the present invention include hydrophilic polymers such as hydrocolloids. Examples of suitable hydrocolloids include alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan, rhamsan, zooglan, methylan, chitin, cyclodextrin, chitosan, and combinations thereof. In certain embodiments of the present invention, xanthan gum is the structuring agent.

Xanthan gum is a high molecular weight natural carbohydrate, specifically, a polysaccharide. One xanthan gum that is suitable for use in the present invention is a high molecular weight polysaccharide produced by *Xanthomonas campestris*. Techniques and strains for producing this polysaccharide are described in U.S. Pat. Nos. 4,752,580 and 3,485,719, the disclosures of which are hereby incorporated by reference. In one embodiment, the xanthan gum may have a viscosity in a one percent salt solution of from about 1000 to about 1700 cP (mPa-sec), as measured at 25° C. with an LV model Brookfield Synchro-Lectric viscometer at 60 rpm, no. 3 spindle. Suitable xanthan gums are available from, for example, CP Kelco, under the tradename, "Keltrol," "Keltrol TF," and "Keltrol 1000."

A swelling agent, when exposed to an appropriate aqueous environment, expands without forming a network system. Pregelatinized starch is a particularly good swelling agent. Pregelatinized starch, also known as "instantized" starch, is precooked so that it swells and begins to thicken instantly when added to cold water. One particularly suitable pregelatinized starch is prepared from modified, stabilized and waxy, maize food starch, and is commercially available from National Starch Company as "INSTANT STARCH, ULTRASPERSE-M." Other suitable swelling agents include, but are not limited to microcrystalline cellulose and/or hydroxypropylmethylcellulose.

In one embodiment, the suspending system is comprised of a xanthan gum structuring agent with a pregelatinized starch swelling agent. In another embodiment, the suspending system is comprised of, based upon the total weight of the liquid suspension dosage form, from about 0.01 percent to about 1 percent or from about 0.05 percent to about 0.40 percent of xanthan gum and from about 1 percent to about 10 percent or from about 0.5 percent to about 3.0 percent of a pregelatinized starch such as that commercially available from National Starch Company under the tradename, "INSTANT STARCH, ULTRASPERSE-M."

In embodiments wherein the dosage form is in a liquid form, e.g., suspension or elixir, the pH of the liquid dosage form should be optimized to minimize the solubility and maximize the chemical stability of any uncoated active ingredient contained therein. In one embodiment wherein the uncoated active agent is basic, e.g., calcium carbonate, the pH of the dosage form may be as close as possible to 2 pH units above the pKa of that basic uncoated active agent. In embodiments wherein the uncoated active agent is acidic, e.g., ibuprofen, the pH of the dosage form may be as close as possible to 2 pH units below the pKa of that acidic uncoated active agent. In certain embodiments employing ibuprofen as the uncoated active agent, the pH of the dosage form may be in the range from about 1.0 to about 5.0, e.g., from about 1.0 to about 4.0.

The dosage form can be buffered using known pH adjusting agents to maintain the pH of the suspension in the desired pH range. Suitable pH-adjusting agents may be present in the dosage form in amounts sufficient to provide the desired degree of pH buffering. The pH-adjusting agents will typically be present in the range of from about 0 to about 1 gram per 100 mL of the dosage form.

In an embodiment containing ibuprofen as the uncoated active agent and a suspending system having alkaline polymers, such as for example sodium carboxymethylcellulose, the pH adjusting agent may be selected from weak organic acids, such as citric acid, malic acid, glutamic acid, and the like having acceptable taste characteristics for use in taste masked oral suspensions.

In one embodiment, the dosage form may optionally contain antimicrobial preservatives having an activity within the desired pH range of the dosage form. Preservatives useful in such pharmaceutical suspensions include, but are not limited to, sodium benzoate, potassium sorbate, salts of edetate (also known as salts of ethylene diaminetetraacetic acid, or EDTA, such as, disodium edetate) and parabens (such as, methyl, ethyl, propyl and butyl p-hydroxybenzoic acids esters). The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art.

In certain optional embodiments, the dosage form of the invention may employ a surfactant for use as a wetting agent to aid in the dispersion of certain hydrophobic active agents. In certain other embodiments, the dosage form of the invention may be substantially free of surfactant. As used herein, "substantially free of surfactant" shall mean that the suspension contains less than about 0.1%, e.g., less than about 0.05% of a surfactant. Examples of suitable surfactants include, but are not limited to sorbitan oleate esters, such as polyoxyethylene sorbitan monooleate also known as polysorbate 80.

In one embodiment, the dosage form is in the form of an aqueous pharmaceutical suspension composition and is comprised of, based upon the total weight of active ingredient per volume (w/v or g/100 ml) of the aqueous pharmaceutical suspension, from greater than about 0 percent to about 30 percent, e.g. about 0.05 percent to about 20 percent, or about 0.5 percent to about 10 percent, or about 0.5 percent to about 5 percent, of the first active ingredient and from greater than about 0 percent to about 10 percent, e.g. about 0.01 percent to about 10 percent, or about 0.03 percent to about 5 percent, of the second, modified release active ingredient.

In another embodiment wherein the first active ingredient is ibuprofen, the amount of first active ingredient in the immediate release portion of the suspension dosage form is, based upon the total weight of first active ingredient per volume (w/v) of the aqueous suspension dosage form, from about 25 to about 400 mg, e.g. from about 50 mg to about 200 mg per teaspoonful of aqueous suspension dosage form, or is about 20 mg of first active ingredient per 1 mL of the aqueous suspension dosage form, which is equivalent to, based upon the total weight of first active ingredient per volume (w/v) of the aqueous suspension dosage form, from about 0.25 percent to about 4 percent, and the second active ingredient is phenylephrine or pseudoephedrine, the amount of second active ingredient in the modified release portion of the suspension dosage form is, based upon the total weight of second active ingredient per volume (w/v) of the aqueous suspension dosage form, from about 1 mg to about 20 mg, e.g. from about 1 mg to about 10 mg per teaspoonful of aqueous suspension dosage form, or is about 1.5 mg of second active ingredient per 1 mL of the aqueous suspension dosage form, which is equivalent to, based upon the total weight of second active ingredient per volume (w/v) of the aqueous suspension dosage form, from about 0.01 percent to about 0.3 percent.

One embodiment of the present invention is directed to a liquid measurable suspension composition that includes, based upon the total weight of the suspension: a) from about 0.05 percent to about 40 percent of a first, immediate release active ingredient; b) from about 20 percent to about 80 percent of water; c) from about 0.1 percent to about 10 percent of a suspending system; d) from about 0 percent to about 40 percent, e.g. from about 20 percent to about 40 percent of a sweetening agent; e) from about 0 percent to about 0.5 percent of excipients; and from about 0.01 percent to about 10 percent of a second portion of modified release particles.

In another embodiment, the dosage form of the present invention comprises, based upon the total weight of the dosage form, from about 0.1 percent to about 10 percent, e.g. from about 0.1 to about 5 percent of the first, immediate release portion; and from about 0.05 percent to about 10 percent, e.g. from about 0.05 percent to about 5 percent, of the second, modified release portion. In one embodiment, the second, modified release portion of the dosage form is comprised of, based upon the total dry weight of the second portion, from about 5 percent to about 80 percent, e.g. from about 5 percent to about 70 percent, of the first, semi-permeable coating layer; from about 10 percent to about 90 percent, e.g., from about 10 percent to about 80 percent of the second protective coating layer; and from about 1 percent to about 50 percent, e.g., from about 1 percent to about 30 percent of the drug-resin complex particles.

According to the present invention, the dosage form contains, based upon the total weight of the dosage form, from about 0.1 percent to about 5 percent, e.g., from about 0.5 percent to about 3 percent, of the first active ingredient; and from about 0.005 percent to about 1 percent, e.g., from about 0.01 percent to about 0.5 percent of the second active ingredient.

In certain embodiments, the viscosity of the suspension of the present invention may range from about 400 cps to about 1500 cps as measured by a Brookfield DV-I+ Viscometer using a #31 spindle and speed of 12 rpm under temperature conditions of about 25° C.

The dosage forms of the present invention are intended to deliver an effective amount of a first active ingredient, such as an NSAID, which has an ATDAIRD of about 5, in the same dosage form as an effective amount of a second active ingredient, such as phenylephrine or psuedoephedrine, which as has an ATDAIRD of about 3 in one administration such that both active ingredients can be released from the dosage form throughout the longer ATDAIRD period.

An "effective amount" of an analgesic is one that provides relief from pain in a patient. For example, a typical adult dose of ibuprofen may range from about 2.9 to about 12 mg/kg weight of the patient given every 4 to 6 hours, for a typical daily dose ranging from about 11.6 to about 72 mg/kg/day. Therefore, administration of an effective amount of ibuprofen to a typical 70 kg adult may involve once or twice daily administration of about 5 ml to about 60 ml of the formulation of the present invention containing, for example, 40 mg/ml ibuprofen. A typical pediatric dose of ibuprofen may range from about 5 to about 10 mg/kg given every 4 to 6 hours, for a typical daily dose ranging from about 20 to about 60 mg/kg/day. Administration of an effective amount of ibuprofen to a typical 15 kg child may involve once or twice daily administration of about 5 ml to about 60 ml of the formulation of the present invention containing, for example, 20 mg/ml ibuprofen.

An "effective amount" of a decongestant is one that provides effective relief of congestion, i.e. a medication that breaks up congestion, as that of the nasal passages and/or sinuses, by reducing swelling. For example, a typical adult dose of phenylephrine may range from about 0.14 to about 0.29 mg/kg weight of the patient given every 6 hours, or about 10 mg to about 20 mg given every 6 hours for a typical adult, with a typical daily dose ranging from about 0.60 to about 1.0 mg/kg/day, or about 0.86 mg/kg/day or about 60 mg phenylephrine per day for the typical adult. Therefore, administration of an effective amount of phenylephrine to a typical 70 kg adult may involve once to four times daily administration of about 2.5 ml to about 10 ml, or about 5 mL, of a formulation of the present invention containing, for example, 3 mg/ml phenylephrine. A typical pediatric dose of phenylephrine may range from about 0.25 to about 0.75 mg/kg given every 2 to 4 hours, or about 3.75 mg to about 11.25 mg given every 6 hours for a typical child, for a typical daily dose ranging from about 1.0 to about 2.7 mg/kg/day, or about 2 mg/kg/day, or about 30 mg of phenylephrine per day for the typical child. Administration of an effective amount of phenylephrine to a typical 15 kg child may involve once to four times daily administration of about 2.5 ml to about 10 ml of the formulation of the present invention containing, for example, 1.5 mg/ml phenylephrine.

In one embodiment, the oral administration of the dosage forms of the present invention provides the user with the first active ingredient, such as NSAIDs, in a modified release dose that continues to release the second active ingredient from the dosage form so that the duration of its therapeutic effect is comparable to that of the first active ingredient.

In one embodiment, the liquid dosage form contains an immediate release portion containing both ibuprofen and phenylephrine, and a modified release portion containing an additional amount of phenylephrine. In this embodiment, the immediate release dose of ibuprofen may range from about 25 mg/5 mL to about 200 mg/5mL of suspension, e.g. about 50 mg/5 mL to about 200 mg/5 mL of suspension, and the immediate release dose of phenylephrine may range from about 2.5 mg to about 15 mg immediate release phenylephrine/5 mL suspension; e.g. about 2.5 mg to about 10 mg immediate release phenylephrine/5 mL suspension. In this embodiment, the modified release dose of phenylephrine may range from about 2.5 mg to about 20 mg modified release phenylephrine/5 ml of suspension; e.g. about 5 to about 15 mg modified release phenylephrine/5 mL suspension.

Another embodiment of the present invention is directed to method for alleviating nasal and respiratory congestion in persons in need thereof with the oral administration of pseudoephedrine or phenylepherine, as well as ameliorating associated conditions such as headache, joint pain, watery nasal passages, weeping eyes, sinus congestion and pain, coughing, excessive exudating of mucus, and bronchitis by way of administering the subject dosage forms of the present invention to such persons.

Beneficially, we have unexpectedly found how to effectively stabilize the release characteristics of the modified release portion of the dosage form throughout the shelf life of the product and throughout the period of treatment, regardless of whether the dosage form is designed as a liquid dosage form, such as a suspension, or as a dry dosage form that can be reconstituted with water prior to administration. Specifically, we have overcome the challenge of preventing active ingredient release from the particles in the product prior to ingestion, while enabling modified release of active ingredient from those same particles in the g.i. fluids.

We further have found how to extend the duration of the therapeutic effect of the second, coated active agent to a duration comparable to that possessed by the uncoated, first active agent by overcoming the interaction between the first active agent and the semi-permeable coating on the second agent.

Advantageously, the formulations of the present invention may be used in a variety of formats including, for example, (i) accurately-measurable single dose dry formulations or liquid suspensions; (ii) multi-dose granular formulations having significant dose flexibility obtainable by measuring different amount of granules to be resuspended on an as-needed basis; (iii) multi-dose liquid suspensions; and (iv) concentrated drops in which the active ingredient is suspended, which is particularly useful in pediatric applications.

In addition, since the formulation is convenient to administer and swallow, and the number of daily doses of active ingredient is reduced, the overall patient compliance is achieved. Additional benefits are anticipated in pediatric practice due to the ease of swallowing and administering.

The following examples further illustrate the invention, but are not meant to limit the invention in any way.

Example 1

Preparation of Phenylephrine—Resin Complex Particles 2125.0 g of phenylephrine hydrochloride was dissolved in 2000.0 g of deionized water in a suitable stainless steel container. 2500.0 g of Amberlite IRP-69 ion exchange resin, commercially available from Rohm & Haas Corporation, was added thereto and stirred using a laboratory mixer at 100 RPM for at least 12 hours. The resulting slurry was filtered through a Wattman #4 filter paper using vacuum filtration. The resulting solid was air dried for 1-2 hours to yield wet resin particles, which were then dried in a Glatt fluid bed GPCG-1 drier for 10 minutes at 50° C. The resulting dry particles contained approximately 32.0% phenylephrine. The remaining, unbound phenylephrine remained in the filtered slurry solution.

Example 2

Preparation of Ethylcellulose Semipermeable First Coating Solution

A coating solution was prepared by dispersing 690 grams of ethylcellulose, which is commercially available from Dow Chemical Corporation under the tradename, "Ethocel 10 CPS," 150 g of acetyltributyl citrate (ATBC), and 20 mg of magnesium stearate USP in a solvent containing, based upon the total weight of the solvent, 3780 g of acetone and 3780 g of isopropyl alcohol (a 50:50 mixture) under ambient conditions. The solution was mixed using a laboratory mixer at 75 RPM for at least 60 minutes.

The resulting coating solution contained, based upon the total wet coating solution, 8.19% of ethylcellulose, 1.78% acetyltributyl citrate, 0.24% magnesium stearate, 44.89% acetone, and 44.89% isopropyl alcohol. The solution contained 10% solids. The relative amounts of solids were, based upon the total weight percent of the dried coating solution, 80.23% ethylcellulose, 17.44% ATBC, and 2.33% magnesium stearate.

Example 3

Preparation of Protective (Enteric), Second Coating Solution

A coating solution was prepared by dispersing 4193.1 g of methacrylate copolymer dispersion (30% solids), commercially available under the tradename, "Eudragit L30D-55," which is commercially available from Rohm Pharma, in 2396.0 g purified water, and mixed at 25 RPM under ambient conditions for 5 minutes. 50.8 g of glycerol monostearate and 126.8 g of triethylcitrate were added thereto with mixing at 50 RPM for at least 30 minutes.

The resulting coating solution contained, based upon the total wet coating solution, 61.97% of Eudragit L30D-55 (30% of which are as solids), 0.75% glycerol monostearate, 1.87% triethylcitrate and 35.41% purified water.

The relative amounts of solids were, based upon the total weight percent of the dried coating solution, 87.63% Eudragit L30D-55, 3.53% glycerol monostearate, and 8.83% of triethylcitrate.

Example 4

Preparation of Drug-Resin Phenylephrine Complex Coated with a Single, Semipermeable Ethylcellulose Layer 1000.0 grams of the drug-resin complex particles from Example 1 were placed into a Glatt GPCG-1/3 coating unit and coated with the ethylcellulose coating solution prepared in accordance with Example 2 by spraying the solution at a rate of about 15.0 g/min under product temperature conditions of about 37-42° C., with an atomization air pressure of approximately 2 bar. The resulting coated phenylephrine granules contained, based upon the total dry weight of the coated phenylephrine granules, about 47.9% of the semipermeable coating.

Example 5

Preparation of Drug-Resin Phenylephrine Complex Coated with an Semipermeable Layer and an Outer Enteric Layer 750.0 grams of the coated phenylephrine particles prepared in accordance with Example 4 were placed into a Glatt GPCG-1/3 coating unit and coated with the enteric Eudragit L30D coating solution prepared in accordance with Example 3 by spraying the solution at a rate of about 15.0 g/min under product temperature conditions of about 54-71° C., and with an atomization air pressure of approximately 2 bar. The resulting coated phenylephrine granules contained, based upon the total dry weight of the double-coated phenylephrine granules, about 65.7% of the outer, protective enteric coating. The amount of ingredients in the final dried, double-coated particles are shown in Table 1.

TABLE 1

Dried Coated Particle Formulation

| Ingredients | Tradename | Percent % (w/w) |
|---|---|---|
| Phenylephrine HCl | | 5.7 |
| Amberlite Drug Resin | Amberlite IRP-69 | 12.0 |
| Eudragit L30D-55 (Enteric polymer) | | 57.6 |
| Ethylcellulose | Ethocel 10 CPS | 13.2 |
| Acetyltributyl citrate | | 3.0 |
| Glycerol Monostearate | | 2.3 |
| Triethyl Citrate | | 5.8 |
| Magnesium Stearate | | 0.4 |
| TOTAL | | 114.5g/100 mL |

Example 6

Production of the Suspension Base Containing Immediate Release Ibuprofen Dose

TABLE 2

Components of Suspension Base

| Ingredients | Tradename | Weight (g)/ 100 mL | Batch Weight (g) for 2 Liter Batch |
|---|---|---|---|
| Purified Water, USP* | | 65.0 | 1300.0 |
| Pregelatinized Starch | Ultrasperse M | 1.50 | 30.0 |
| Xanthan Gum, NF | Xantural 180 | 0.180 | 3.60 |
| Glycerin, USP | | 10.0 | 200.0 |
| Sucrose, NF | Bottler's Floc Free | 30.0 | 600.0 |
| Polysorbate 80 K NF | | 0.050 | 1.00 |
| Citric Acid, Anhydrous, USP | | 0.180 | 3.60 |
| Acesulfame K | | 0.100 | 2.00 |
| Ibuprofen USP | | 2.00 | 40.0 |
| Purified Water, USP, q.s. to 100 mL | | 5.49 | 109.8 |
| TOTAL | | 114.5g / 100 mL | 2290.0 |

*Sterile Water for Irrigation USP

As indicated in Table 2 above, 1300.0 g of purified water USP were charged into a mixing tank equipped with a Scott Turbon high shear mixer and mixed at about 500 rpm to about 1000 rpm in order to create a good vortex. The pregelatinized starch and xanthan gun were then added to the mixing tank and mixed for 20 minutes. The glycerin was then added thereto and mixed for 5 minutes. The sucrose was then added thereto and mixed for 12 minutes. The polysorbate-80 NF, citric acid anhydrous USP and acesulfame K were added sequentially, and then the resulting mixture was mixed for 10 minutes. The ibuprofen USP was added to the batch and mixed for 20 minutes at about 500 rpm and 1000 rpm. The remainder of the purified water was then added thereto and mixed for 10 minutes.

Example 7

Production of the Suspension Containing Immediate Release Ibuprofen Dose and a Phenylephrine-Resin Complex Coated with a Single Semipermeable Layer 600 mg of the coated phenylephrine particles prepared in accordance with Example 4 were added to a suitable 100 mL volumetric flask and diluted to a 100.0 mL volume with the suspension base prepared according to Example 6, then mixed end-over-end manually until the resulting suspension was visually homogenous. The resulting suspension contained 100 mg/5 mL of the immediate release ibuprofen dose and 5 mg/5 mL of the phenylephrine dose Example 8

Production of the Suspension Containing Immediate Release Ibuprofen Dose and a Phenylephrine-Resin Complex Coated with a Semipermeable Layer and an Outer Protective Enteric Layer 1724.0 mg of the coated phenylephrine prepared in accordance with Example 5, which contained 5.7% of active phenylephrine HCl, was added to a suitable 100 mL volumetric flask. The resulting suspension was then diluted to 100.0 mL volume with suspension base as prepared according to Example 6 and mixed end-over-end manually until the resulting suspension was homogeneous. The resulting final suspension contained 100 mg/5 mL of the immediate release ibuprofen dose and 5 mg/5 mL of the modified release phenylephrine dose.

Example 9

Dissolution Analysis of the Suspension of Example 7 and Example 8

Dissolution Media:
pH 1 (0.1N HCl) Media:
1000 mL of 0.1N HCl was placed in each of three containers of a USP Type II apparatus with paddles. A 5.0 mL sample of the final suspension produced in Example 7 was then independently added to each of the three containers and mixed at a speed of 50 r.p.m. at 37° C. until the mixture was visually homogeneous.

This procedure was repeated, but with the substitution of the sample from Example 7 with a sample from Example 8.

This procedure was also repeated two additional times, but with the substitution of about 20.5 mg of particles from Example 4 and about 133.0 mg of particles from Example 5, respectively. These were calculated based on a dose of about 4.1 mg phenylephrine as a free base.

1 Hour pH Change Media:
750 mL of 0.1N HCl was placed in each of three additional containers of a USP Type II apparatus with paddles. A 5.0 mL sample of the final suspension produced in Example 7 was then independently added to each of the three containers and mixed at a speed of 50 r.p.m at 37° C. until the mixture was homogeneous. After 1 hour, a 10 ml sample was removed from the vessel, then 250 mL of 0.2M $Na_3PO_4$ was added thereto, which changed the media composition to about 990 mL of 0.05M sodium phosphate buffer at a pH of about 6.8.

This procedure was repeated, but with the substitution of the sample from Example 7 with a sample from Example 8.

This procedure was then also repeated two additional times, but with the substitution of about 20.5 mg of particles from Example 4 and about 133.0 mg of particles from Example 5, respectively. These were calculated based on a dose of about 4.1 mg phenylephrine as a free base.

pH 7.2 (Phosphate Buffer) Media:
1000 mL of 0.05M $KH_2PO_4$ buffer, adjusted to pH 7.2 with NaOH, was placed in each of three additional containers of a USP Type II apparatus with paddles. A 5.0 mL sample of the final suspension produced in Example 7 was then independently added to each of the three containers and mixed at a speed of 50 r.p.m. at 37° C. until the mixture was visually homogeneous.

This procedure was repeated, but with the substitution of the sample from Example 7 with a sample from Example 8.

This procedure was also repeated two additional times, but with the substitution of about 20.5 mg of particles from Example 4 and about 133.0 mg of particles from Example 5, respectively. These values were calculated based on a dose of about 4.1 mg phenylephrine as a free base.

Sampling and Analysis:
After 1, 2, 3, 4, 6, 7, and 8 hours, respectively, thereafter, 10 mL samples of the suspension/buffer mixture were independently removed from each of the containers.

Each 10 mL sample was then independently analyzed for ibuprofen and phenylephrine content using a high pressure liquid chromatograph (HPLC) equipped with a Waters® Alliance 2695 Separations Module and a Waters® 2996 PDA detector set at a wavelength of 270 nm in order to derive dissolution curves for phenylephrine and ibuprofen at 1, 2, 3, 4, 6, 7, and 8 hours, respectively. Each of the dissolution samples was compared to a mixed standard containing phenylephrine (free base) at 0.004 mg/mL and ibuprofen (free acid) at 0.10 mg/mL, which correlated to the theoretical concentration required for 100% release of phenylephrine free base and ibuprofen free acid.

The mobile phase used in the HPLC was prepared using 20 mM Sodium Dodecyl Sulfate (SDS) in 0.2% $H_3PO_4$/Methanol/Acetonitrile (40/35/25). The injection volume was 50 μL with a run time of approximately 10 minutes and a pump flow of 1.0 mL/min. The column used for analysis was a Phenomenex Luna C8(2), 3 μm, 4.6×75 mm.

The results of the HPLC analysis are illustrated in FIGS. 1 to 4, with each graphed point representing an average of the percent phenylephrine dissolved in the three vessels.

Figure 1:
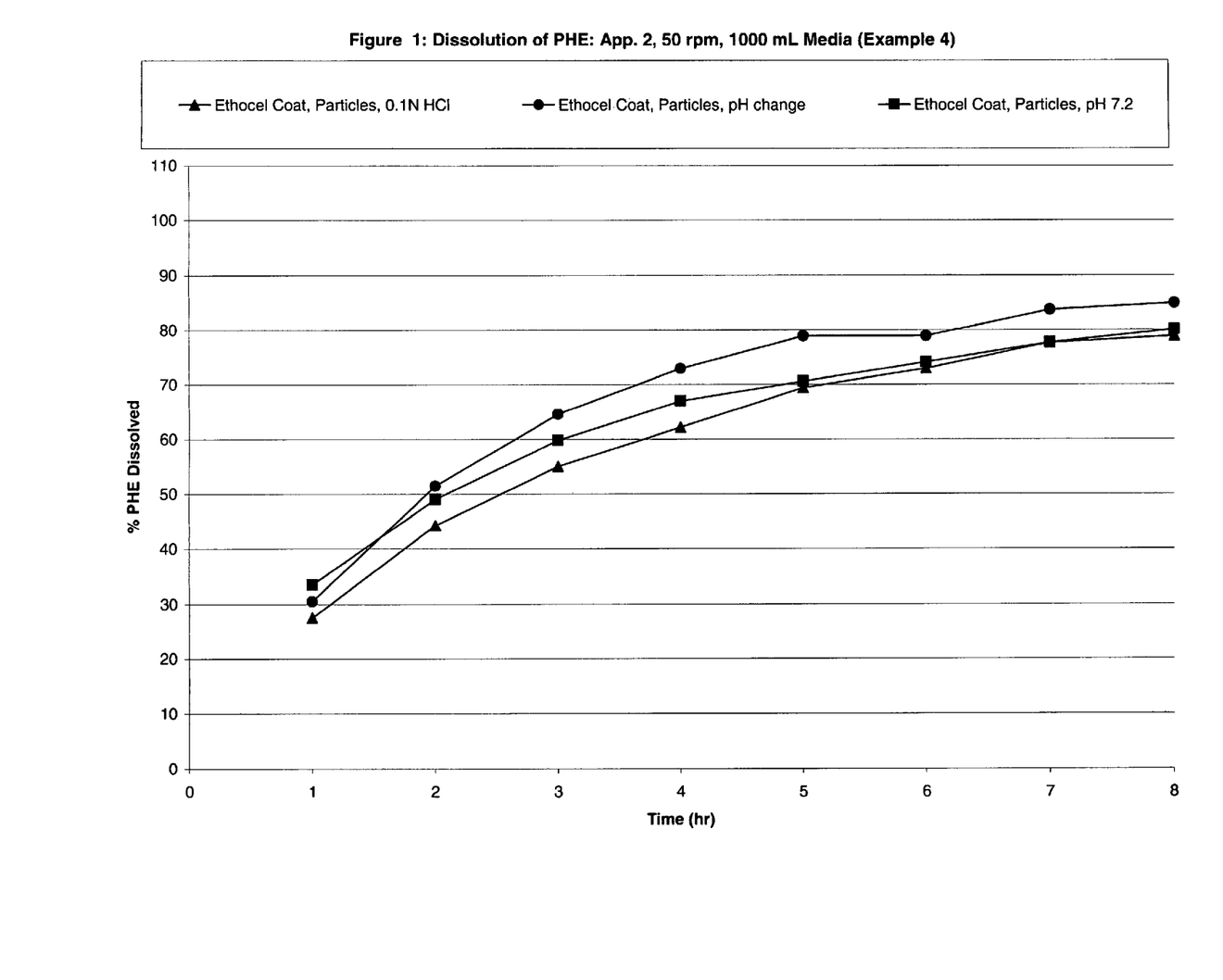
FIG. 1 depicts the percentage released (i.e. dissolution) of phenylephrine in particles coated with an ethylcellulose semipermeable coating layer as prepared in accordance with Example 4 versus time in three different media.
Figure 2:
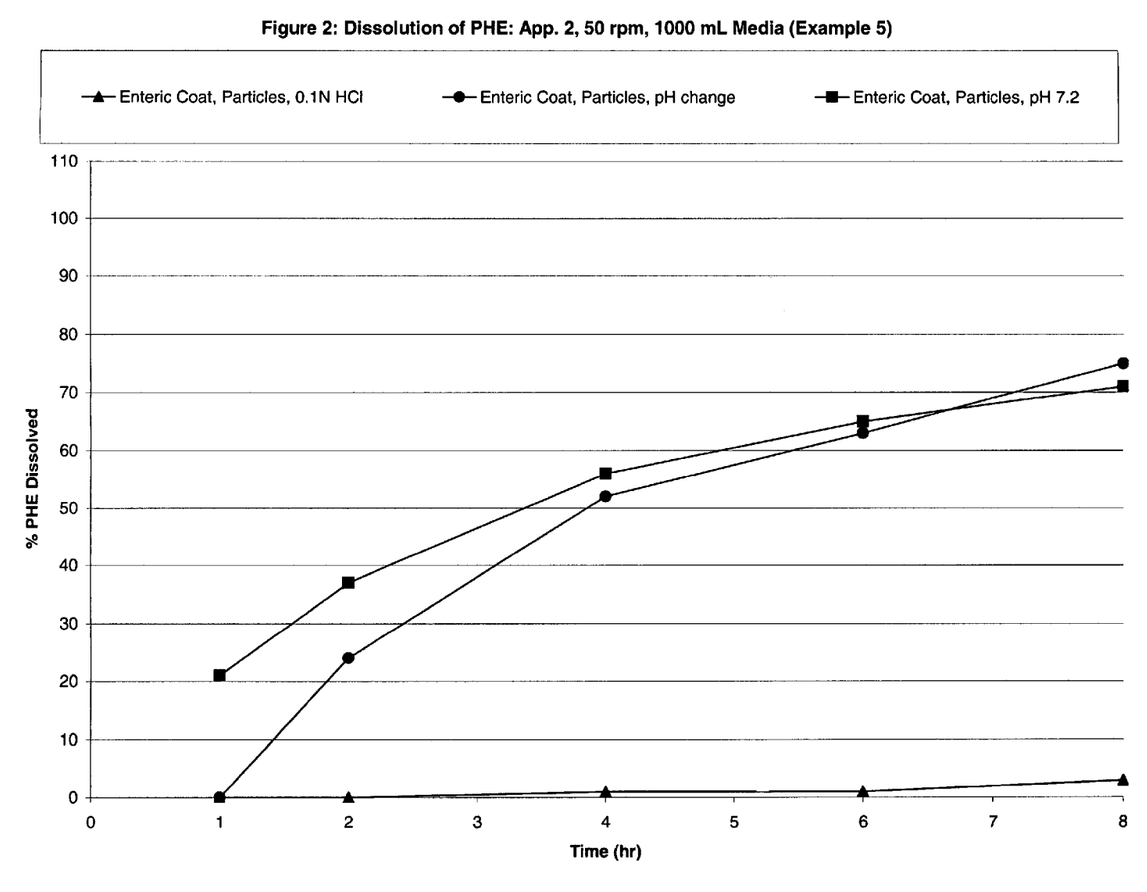
FIG. 2 depicts the percentage released (i.e. dissolution) of phenylephrine in particles coated with an ethylcellulose semipermeable coating layer and an exterior enteric coating layer as prepared in accordance with Example 5 versus time in three different media.
Figure 3:
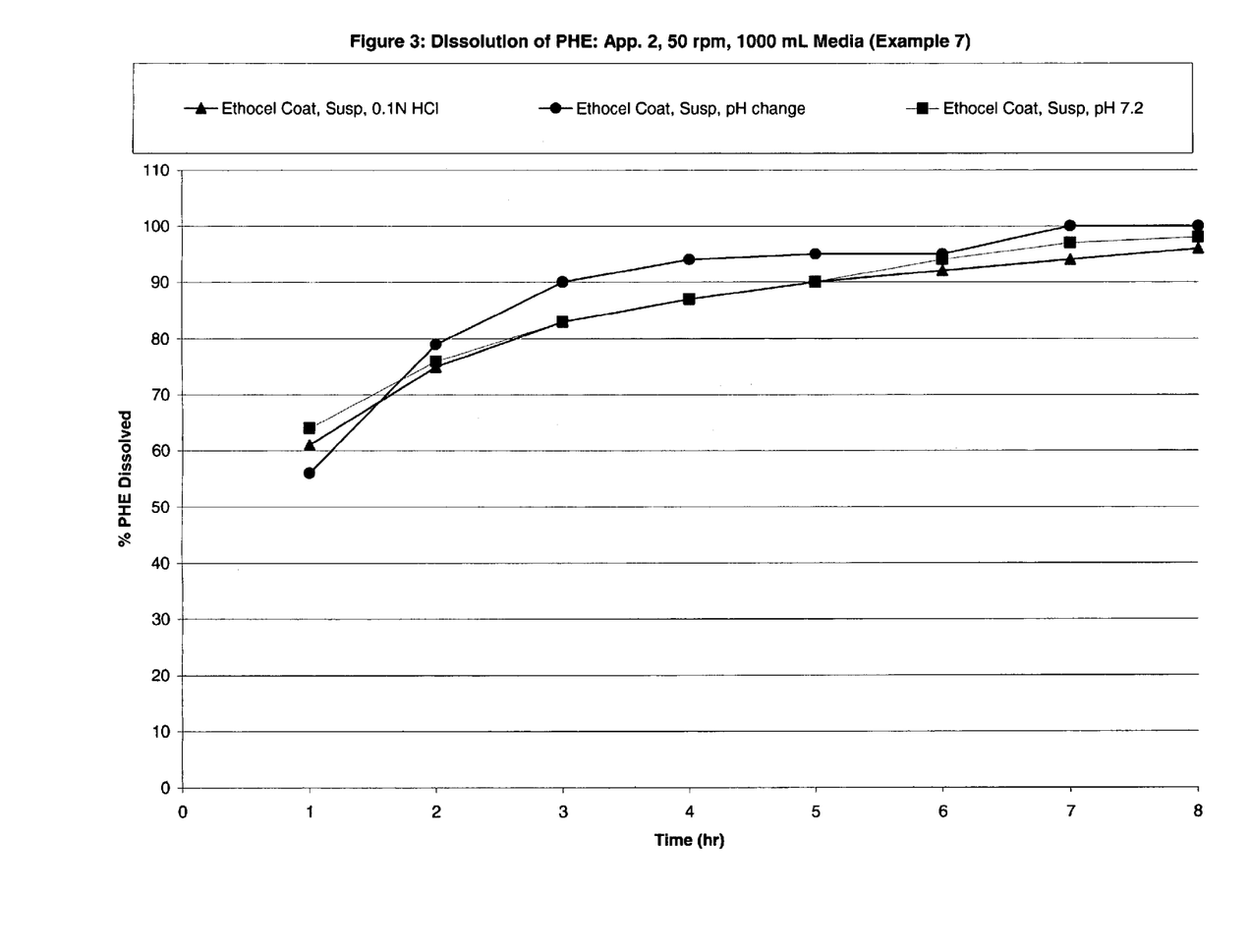
FIG. 3 depicts the percentage released (i.e. dissolution) of phenylephrine in particles coated with an ethylcellulose coating layer in a suspension containing immediate release ibuprofen as prepared in accordance with Example 7 versus time.
Figure 4:
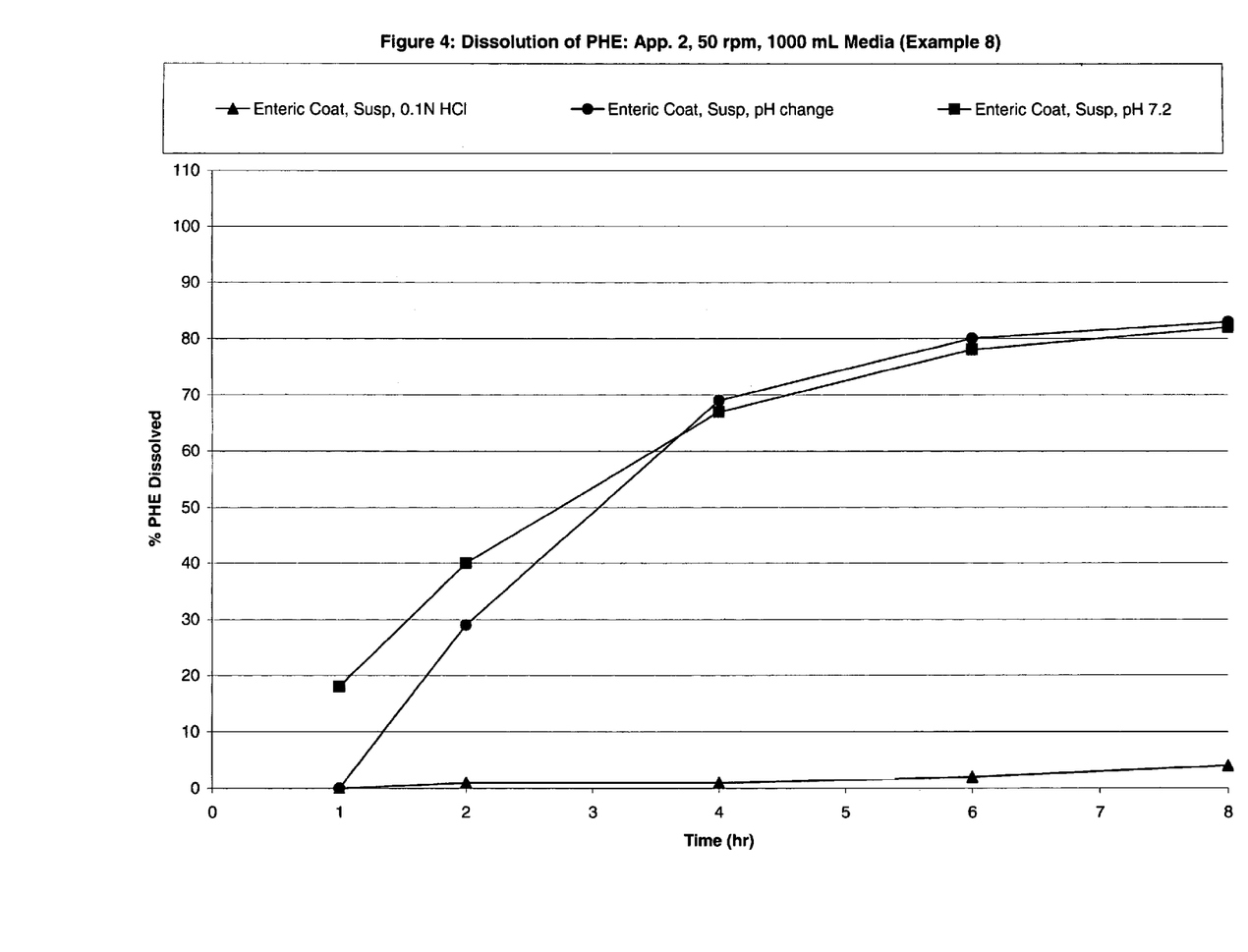
FIG. 4 depicts the percentage released (i.e. dissolution) of phenylephrine in particles coated with an ethylcellulose coating layer and an exterior enteric coating layer in suspension containing immediate release ibuprofen as prepared in accordance with Example 8 versus time.

A comparison of FIGS. 1 and 3 showed that the phenylephrine release rate from the ethylcellulose coated particles increased substantially when the particles were placed into an ibuprofen-containing suspension. By contrast, a comparison of FIGS. 2 and 4 showed that the phenylephrine release rate from the particles coated with an inner layer of ethylcellulose and an outer layer of enteric polymer remained substantially the same when the particles were placed into an ibuprofen-containing suspension.

We claim:

1. A liquid pharmaceutical dosage form comprising:
   a) a first portion comprising ibuprofen and/or pharmaceutically acceptable salts thereof, wherein said ibuprofen is released from the dosage form in a substantially immediate manner upon contact of the dosage form with a dissolution medium; and
   b) a second portion comprising:
      i. a phenylephrine-ion exchange resin complex, said phenylephrine-ion exchange resin complex comprising phenylephrine complexed with a sulfonated co-polymer of styrene and divinylbenzene;
      ii. a first coating layer comprising a semi-permeable coating comprising a polymer selected from the group consisting of cellulose acetate, ethylcellulose, non-enteric polymethacrylates and copolymers and mixtures thereof, wherein said semi-permeable coating substantially covers said phenylephrine-ion exchange resin complex; and
      iii. a second coating layer comprising a protective coating, wherein said second coating layer covers said first coating layer,
   wherein said phenylephrine is released from the dosage form in a substantially sustained release manner.

2. The dosage form of claim 1, further comprising a liquid medium for the administration of the first portion and the second portion.

3. The dosage form of claim 2, wherein the liquid medium comprises agents selected from the group consisting of solvents, structuring agents, swelling agents, suspending systems, surfactants, sweeteners, buffering agents, preservatives, bacteriostatic agents, colorants, flavoring agents, and mixtures thereof.

4. The dosage form of claim 2 wherein the liquid medium is water.

5. The dosage form of claim 2 wherein the liquid medium is mixtures of water with a pharmaceutically acceptable water-miscible co-solvent selected from the group consisting of glycols, alcohols, glycerol, and mixtures thereof.

6. The dosage form of claim 1, wherein the weight ratio of the first coating layer to the second coating layer is about 10:90 to about 90:10.

7. The dosage form of claim 1, wherein the second portion comprises, based upon the total dry weight of the second portion,
   a) from about 5 percent to about 80 percent of the first coating layer;
   b) from about 10 percent to about 90 percent of the second coating layer; and
   c) from about 1 percent to about 50 percent of the phenylephrine-ion exchange resin complex.

8. The dosage form of claim 1, further comprising, based upon the total weight of the dosage form, from about 0.1% to about 5% of the first portion; and from about 0.05% to about 5% of the second portion.

9. The dosage form of claim 1 further comprising, based upon the total weight of the dosage form,
   a) from about 0.1% to about 5% of-ibuprofen; and
   b) from about 0.005% to about 1% of phenylephrine.

10. A method for treating pain in a mammal in need thereof, comprising administering the dosage form of claim 1 in an amount effective for providing pain relief to the mammal for a time period of at least about four hours to about six hours after administration of the dosage form.

11. A method for treating sinus congestion in a mammal in need thereof, comprising administering the dosage form of claim 1 in an amount effective for providing sinus congestion relief to the mammal for a time period of at least about four hours to about six hours after administration of the dosage form.

12. The dosage form of claim 1, wherein said non-enteric polymethacrylates are selected from the group consisting of poly(ethyl acrylate, methyl methacrylate) 2:1; poly(methyl acrylate, methyl methacrylate, methacrylic acid) 7:3:1; poly(ethyl acrylate, methyl methacrylate, triethylammonioethyl methacrylate chloride) 1:2:0.2; poly(ethyl acrylate, methyl methacrylate, triethyleammonioethyl methacrylate chloride 1:2:0.1, and copolymers and mixtures thereof.

13. The dosage form of claim 1, wherein the semi-permeable coating comprises a polymer selected from the group consisting of cellulose acetate, ethylcellulose, and mixtures thereof.

14. The dosage form of claim 1, wherein the protective coating comprises a polymer selected from the group consisting of poly(methacrylic acid, methyl methacrylate) 1:2; poly(methacrylic acid, methyl methacrylate) 1:1; and poly(methacrylic acid, ethyl acrylate) 1:1.

15. The dosage form of claim 1, wherein the protective coating comprises a polymer selected from the group consisting of hydroxypropyl methylcellulose phthalate, hydroxypropyl methylcellulose acetate succinate, cellulose acetate phthalate, polyvinylacetate phthalate, shellac and copolymers and mixtures thereof.

16. The dosage form of claim 1, wherein the protective coating comprises a material selected from the group consisting of a fatty acid ester, a wax, or mixtures thereof.

17. The dosage form of claim 16, wherein the fatty acid ester is selected from the group consisting of sucrose fatty acid esters; mono-di- and triglycerides; glyceryl behenate; glyceryl palmitostearate; glyceryl tristearate; glyceryl trilaurylate; glyceryl myristate; lauroyl macrogol-32 glycerides; stearoyl macrogol-32 glyceride; fatty acid esters having a fatty acid chain length of about $C_{10}$-$C_{40}$; and mixtures thereof.

* * * * *